United States Patent
Terada et al.

(10) Patent No.: US 6,391,443 B1
(45) Date of Patent: May 21, 2002

(54) POLYETHYLENE COMPOSITE FIBER AND A NON-WOVEN FABRIC USING THE SAME

(75) Inventors: Hirokazu Terada; Yukinori Kataoka, both of Shiga (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/866,469

(22) Filed: May 29, 2001

(30) Foreign Application Priority Data

May 29, 2000 (JP) ........................................ 2000-158451
May 29, 2000 (JP) ........................................ 2000-158452

(51) Int. Cl.$^7$ .............................. D01F 8/00; D01F 8/06
(52) U.S. Cl. ........................ 428/370; 428/373; 428/374
(58) Field of Search ................................. 424/370, 373, 424/374; 526/348.3; 442/362, 364

(56) References Cited

U.S. PATENT DOCUMENTS

| | | | |
|---|---|---|---|
| 5,444,145 A | * | 8/1995 | Brant et al. ............... 526/348.3 |
| 5,540,992 A | * | 7/1996 | Marcher et al. ............ 428/373 |
| 5,693,420 A | * | 12/1997 | Terada et al. ............... 428/370 |
| 5,866,488 A | * | 2/1999 | Terada et al. ............... 442/362 |

FOREIGN PATENT DOCUMENTS

| | | |
|---|---|---|
| JP | 58-191215 | 11/1983 |
| WO | 93/01334 | 1/1993 |

* cited by examiner

*Primary Examiner*—Newton Edwards
(74) *Attorney, Agent, or Firm*—McDermott, Will & Emery

(57) ABSTRACT

This invention relates to a polyethylene composite fiber comprising two kinds of polyethylene resin components having different melting points and a non-woven fabric using the same, wherein the low melting component (A) comprises a polyethylene (a) polymerized with a metallocene catalyst, and having a density of 0.850 to 0.930 g/cm$^3$ and a Q value (number average molecular weight/weigh average molecular weight) of 3.0 or less, and the high melting component (B) is a polyethylene (b) having a density of 0.940 g/cm$^3$ or more, and preferably analysis of the fiber using a differential scanning calorimeter (DSC) shows specified thermal property.

The fiber of this invention can be easily processed into a non-woven fabric at a wide range processing temperature, and suitably used for medical materials such as being disinfected under radiation.

17 Claims, 2 Drawing Sheets

POLYETHYLENE COMPOSITE FIBER AND A NON-WOVEN FABRIC USING THE SAME

BACKGROUND

1. Technical Field of the Invention

This invention relates to a polyethylene composite fiber and a non-woven fabric using the same. More specifically, it relates to the polyethylene composite fiber which can be processed into a non-woven fabric within wider processing temperature range, and of which obtained non-woven fabric has good touch feeling and high strength. Further, it relates to the non-woven using the same and a medical or hygienic material using the non-woven.

2. Description of Related Art

Presently, disposable materials made of non-woven for medical use such as surgical caps, surgical sheets, surgical covering clothes, surgical gowns are spreading rapidly. This is to solve a recent problem of hospital infection such as an infection of MRSA (methicillin-resistant *Staphylococcus aureus*), hepatitis or HIV (human immunodeficiency virus). Further, using disposable non-woven materials requires no necessity for cleaning, so that nursing work can be simplified without deteriorating nursing quality. Also it can be one of solutions for a labor shortage that has been becoming serious social problem. The non-woven fabric for medical use is required to have bacteria barrier property, anti-permeability, water repellency, lint free property and so on, but also importantly required to have good wear feeling, strong tenacity and cost performance, because the fabric is directly contacted to human body and disposable for only one time use.

As raw materials of fibers for non-woven, polyethylenes, polypropylenes and polyesters are widely used. Concerning to non-woven fabrics for medical use, it is not exceptional to use these resins generally for the raw materials of the non-woven fabrics.

By the way, the non-woven fabrics for medical use are frequently disinfected under radiation, but it is a problem and restricted to use polypropylene resins for usage such as being disinfected under radiation, because the polymer chain is cut resulted from chemical bonds cut on tertiary carbon atoms under radiation, and the non-woven fabric lose their tenacity drastically.

Concerning to polyester resins, radiation dose not weaken their tenacity, but polyester resins cost higher than polyolefin resins. And when polyester non-woven fabric having high basis weight is used to make the fabric tenacious enough to avoid being torn by user's body action, or to make the fabric being not see-through, the fabric becomes hard and has bad wear feeling, or lacks its light feeling due to the raw material resin's nature. Because of these problems, polyester non-woven fabrics are not positively used by hospital and inhibitedly do not spread.

Contrary to this, polyethylene resins are suitable for medical use non-woven fabrics, because of some advantage such that soft non-woven fabrics can be produced due to the raw material resin's nature, and having no tertiary carbon atoms does not weaken the tenacity under radiation.

However, conventional non-woven fabrics composed of single polyethylene component having no composite structure are not suitable for through-air processing method using heated air to obtain non-woven fabrics, the method makes less softness problem of the non-woven fabric.

To solve this problem, for example, Japanese Tokkyo Kouhyou Koho Hei 6-508892 (corresponding to PCT Gazette W093/01334) discloses a polyethylene composite fiber having a high density polyethylene as the first component and a copolymer of ethylene and á-olefin (abbreviated as "L-LDPE" hereinafter) as the second component. But using general L-LDPE as the second component, it is not sufficiently suitable for processing method such as the through-air method, because the melting point difference between both components is still small. Using a L-LDPE having relatively low density, a very low density polyethylene (VLDPE) or an ultra low density polyethylene (ULDPE) as the second component to increase the melting points difference between the first and second components, but with decreasing of the resin density, there has been presently still some problems that the surface of the fibers being stickier, appearance of neps at carding stage, and the tenacity of obtained non-woven fabrics being decreased considerably.

SUMMARY OF INVENTION

This invention aims to solve the above mentioned problem, and to present a polyethylene composite fiber being usable for thermal-embossing and through-air processing, being possibly used for production of non-woven fabrics having good touch feeling and showing high tenacity, and also to present a non-woven fabric using the same.

The present inventors have diligently made research to solve the above problem of the conventional polyethylene fibers, and have got knowledge that the problem can be solved by a polyethylene composite fiber which comprise a high melting component (B) comprising a polyethylene (b) with specified density, and a low melting component (A) having lower melting point than (B), comprising a polyethylene (a) with specified Q value (number average molecular weight/weigh average molecular weight) polymerized with metalocene catalyst, and have made reduction to practice of this invention.

MEANS TO SOLVE THE PROBLEM

This invention is characterized that;

1. A polyethylene composite fiber comprising two kinds of polyethylene resin components having different melting points, wherein the low melting component (A) comprises a polyethylene (a) polymerized with a metallocene catalyst, and having a density of 0.850 to 0.930 g/cm$^3$ and a Q value (number average molecular weight/weigh average molecular weight) of 3.0 or less, and the high melting component (B) is a polyethylene (b) having a density of 0.940 g/cm$^3$ or more, 2. A polyethylene composite fiber comprising two kinds of polyethylene resin components having different melting points, wherein the low melting component (A) comprises a polyethylene (a) polymerized with a metallocene catalyst, and having a density of 0.850 to 0.930 g/cm$^3$ and a Q value (number average molecular weight/weigh average molecular weight) of 3.0 or less, and the high melting component (B) is a polyethylene (b) having a density of 0.940 g/cm$^3$ or more, and analysis of the fiber using a differential scanning calorimeter (DSC) shows two different endothermic peaks $P_1$ and $P_2$ on the DSC curve from the two components (A) and (B) of the fiber respectively, and when $L_1$ is defined as the length from the baseline of the DSC curve to the endothermic peak $P_1$, and when W is defined as the length of a linear segment parallel with the baseline, passing the midpoint between the baseline and $P_1$, and crossing the DSC curve, the relationship of $L_1$ and W is expressed as $L_1>3W$, on the proviso that a programming rate is 10° C./min., and the DSC chart is so scaled as that the length of 2 W/g scale on the vertical axis (the heat flow scale, unit: W/g) equals to the length of 50° C. scale on the horizontal axis (the temperature scale, unit: ° C.).

3. The polyethylene composite fiber according to the above article 2, wherein $P_3$ is defined as a point being on the DSC curve between the two endothermic peaks $P_1$ and $P_2$ of the two components and being closest to the baseline, and $L_2$ is defined as the length of a linear segment rectangularly lying from the baseline to the point $P_3$, the relationship of $L_1$, and $L_2$ is expressed as $L_1>3L_2$.

4. The polyethylene composite fiber according to the above article 2, wherein the polyethylene (b) of the high melting component (B) is a high density polyethylene having a density of 0.945 g/cm³ to 0.965 g/cm³.

5. The polyethylene composite fiber according to the above article 2, wherein the polyethylene (b) of the high melting component (B) is a polyethylene having a melting point of 125° C. to 135° C.

6. The polyethylene composite fiber according to the above article 2, wherein the polyethylene (b) of the high melting component (B) is a polyethylene having a melt flow index of 5 g/10 min. to 45 g/10 min.

7. The polyethylene composite fiber according to the above article 2, wherein the polyethylene (a) of the low melting component (A) is a polyethylene having a density of 0.850 g/cm³ to 0.930 g/cm³.

8. The polyethylene composite fiber according to the above article 2, wherein the polyethylene (a) of the low melting component (A) is a polyethylene having a melting point of 70° C. to 125° C.

9. The polyethylene composite fiber according to the above article 2, wherein the polyethylene (a) of the high melting component (A) is a polyethylene having a melt flow index of 5 g/10 min. to 45 g/10 min.

10. The polyethylene composite fiber according to the above article 2, wherein the melting point difference of the two components is 5° C. or more.

11. A non-woven fabric using the polyethylene composite fiber according to the above article 1.

12. A non-woven fabric using the polyethylene composite fiber according to the above article 2.

13. The non-woven fabric according to the above article 12, wherein the non-woven fabric is obtainable with spun bonding method.

14. The non-woven fabric according to the above article 12, wherein the non-woven fabric is obtainable with through air processing method that the fiber is thermally melt-bonded one another.

15. The non-woven fabric according to the above article 12, wherein the non-woven fabric is obtainable with point bonding method that the fiber is thermally melt-bonded one another.

16. A medical article using the non-woven fabric according to the above article 12.

17. A sanitary article using the non-woven fabric according to the above article 12.

P1: The endothermic peak of the low melting component (A).

P2: The endothermic peak of the high melting component (B).

P3: The closest Point to the baseline on the DSC curve between the two endothermic peaks $P_1$ and $P_2$.

L1: The length of the linear segment rectangularly lying from the baseline to the point $P_3$.

L2: The length from the baseline of the DSC curve to the endothermic peak $P_1$.

W: The length of the linear segment parallel with the baseline, passing the midpoint between the baseline and $P_1$, and crossing the DSC curve.

Figure 2:
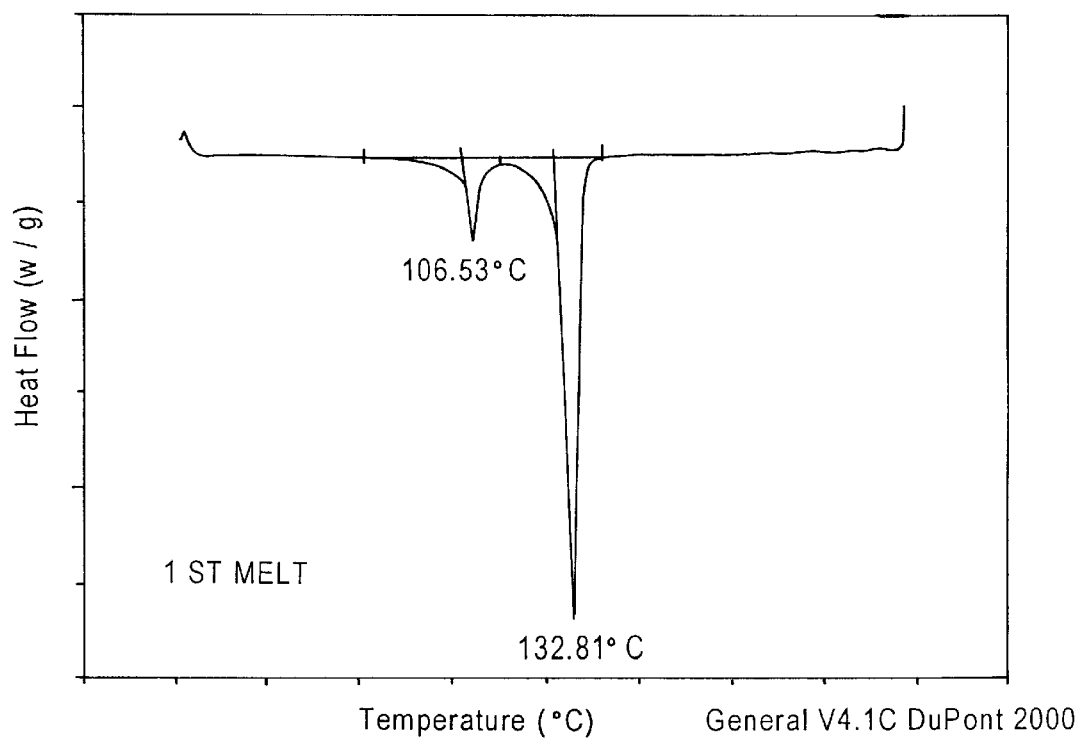

FIG. 2: DSC chart of the polyethylene fiber of this invention comprising the polyethylene polymerized with metallocene catalyst.

Figure 3:
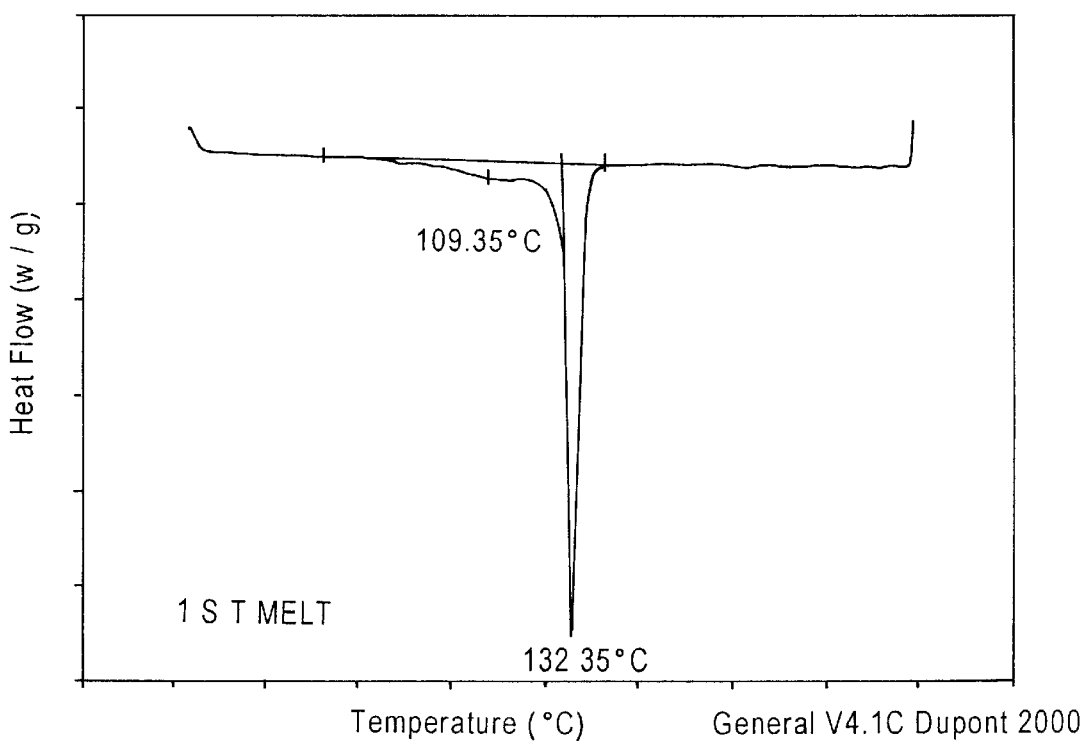

FIG. 3: DSC chart of the polyethylene fiber of this invention comprising a polyethylene polymerized with conventional Ziegler-Natta catalyst.

DETAILED DESCRIPTION OF THE INVENTION

This invention is explained in detail as the following.

The polyethylene composite fiber of this invention is a composite fiber comprising the high melting component (B) and the low melting component (A) having lower melting point than the high melting component (B).

The high melting component (B) comprises a polyethylene (b) having a density of 0.940 g/cm³ or more as the main component. Which can be exemplified as such a polyethylene is a ethylene homo-polymer or a ethylene copolymer polymerized by low pressure method with conventional Ziegler-Natta catalyst, containing 2 weight percent at most of alkene comonomer with C3 to C12 carbon atoms. Preferable density range of this polyethylene is 0.940 g/cm³ to 0.965 g/cm³, and in this density range, a high density polyethylene of 0.945 g/cm³ to 0.960 g/cm³ is more preferable.

The low melting component (A) comprises a polyethylene (a) having a Q value of 3.0 or less as the main component. Which can be exemplified as such a polyethylene is a ethylene copolymer having no substantial long branching chain, usually containing 15 weight percent or less of alkene comonomer with C3 to C12 carbon atoms.

In the case of this polyethylene (a) being polymerized by metallocene catalyst, the melting point can be lowered and the stickiness of the fiber surface can be reduced, comparing with the case of other polyethylene having the same density level polymerized by conventional Ziegler-Natta catalyst. Furthermore, the polyethylene (a) polymerized by metallocene catalyst has narrow molecular weight distribution (small Q value), so that stable fiber spinning is possible, and obtained non-woven fabric is soft and has good touch feeling, also has high adhesion strength and heat-seal strength.

The polyethylene (a) mentioned the above can be obtained using the metallocene catalyst. Typical compound as the metallocene catalyst is such as;
bis(cyclopentadienyl)zirconium dichloride,
bis(cyclopentadienyl)hafnium dichloride,
ethylenebis(indenyl)zirconium dichloride,
ethylenebis(indenyl)hafnium dichloride,
isopropylydene(cyclopentadienyl-9-fluorenyl)zirconium dichloride,
isopropylydene(cyclopentadienyl-9-fluorenyl)hafnium dichloride,
isopropylydene(cyclopentadienyl-2,7-dimethyl-9-fluorenyl) zirconium dichloride,
isopropylydene(cyclopentadienyl-2,7dimethyl-9-fluorenyl) hafnium dichloride,
dimethylsilanediylbis(2,4,5-trimethylcyclopentadienyl) zirconium dichloride,
dimethylsilanediylbis(2,4-dimethylcyclopentadienyl) zirconium dichloride,
dimethylsilanediylbis(2,4,5-trimethylcyclopentadienyl) hafnium dichloride, or
dimethylsilanediylbis(2,4-dimethylcyclopentadienyl) hafnium dichloride.

Among polyethylenes produced with these catalysts, many are commercially available, and preferable one may be selected from those having the specified Q value, melting point and melt flow rate as this invention. Further, it is more effective to select one having more specified range of Q value, melting point and melt flow rate as discussed later.

In this aspect of the polyethylene (a), a linear low density polyethylene having the density range of 0.850 g/cm$^3$ to 0.930 g/cm$^3$ is more preferable. If the density is less than 0.850 g/cm$^3$, the fiber surface is sticker when processed into a fiber, and card proccessability is worsened. Contrary, the density is over 0.930 g/cm$^3$, the melting point difference between the high melting component (B) and the low melting component (A) is not large enough, so that the temperature range at the non-woven processing can not be widened, and the problem is not only worsened proccessability but also the obtained non-woven fabric having bad touch feeling. More preferable density range of the polyethylene (a) is 0.900 g/cm$^3$ to 0.925 g/cm$^3$.

The melting point of the polyethylene (a) is preferably in the range of 70° C. to 125° C. And the MFR (melt flow rate) of the polyethylene (a) is preferably in the range of 5 g/10 min. to 45 g/10 min., further more preferable is the range of 25 g/10 min. to 40 g/10 min.

The Q value of the polyethylene (a) is 3.0 or less, and 2.5 or less is preferable. If the Q value is over 3.0, distribution of low molecular weight fraction is increased, so that the obtained fiber is stickier and lowered adhesion strength.

Figure 1:
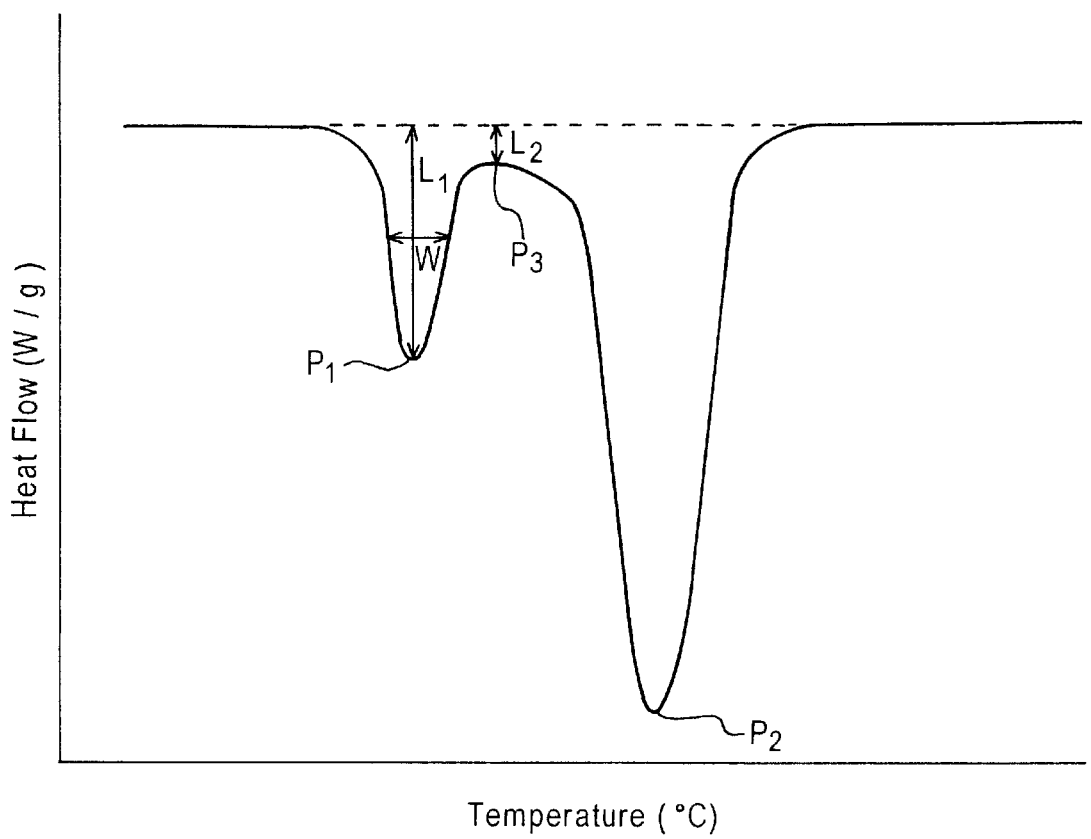
FIG. 1: Model chart for interpreting the differential scanning calorimetry (DSC) curve of the polyethylene fiber of this invention comprising the polyethylene polymerized with metallocene catalyst.

One of preferable aspects of the polyethylene fiber of this invention is that;
analysis of the fiber using a differential scanning calorimeter (DSC) shows two different endothermic peaks $P_1$ and $P_2$ on the DSC curve from the two components (A) and (B) of the fiber respectively,
and when $L_1$ is defined as the length from the baseline of the DSC curve to the endothermic peak $P_1$, and when W is defined as the length of a linear segment parallel with the baseline, passing the midpoint between the baseline and $P_1$, and crossing the DSC curve,
the relationship of $L_1$ and W is expressed as $L_1 > 3W$,
on the proviso that a programming rate is 10° C./min., and the DSC chart is so scaled as that the length of 2 W/g scale on the vertical axis (the heat flow scale, unit: W/g) equals to the length of 50° C. scale on the horizontal axis (the temperature scale, unit: ° C.), as shown on FIG. 1.

Differential scanning calorimetry (DSC) is the most general method to analyze melting point of resin, its melt starting temperature, its proportion of components, and so on. In this invention, the DSC curve of the polyethylene composite fiber preferably meets the above mentioned condition. The DSC curve can be observed according to the analyzing method of JIS (Japanese Industrial Standard) K7122 using the differential scanning calorimeter (DSC). Meeting within the above mentioned condition, the polyethylene fiber of this invention can be easily obtained to be processed into the non-woven fabric under wide processing temperature, and the non-woven fabric shows good touch feeling and high tensile strength.

Within the above mentioned condition, the polyethylene fiber of this invention can take the most preferable aspect in further specified condition that; $P_3$ is defined as a point being on the DSC curve between the two endothermic peaks $P_1$ and $P_2$ from the two components and being closest to the baseline, and $L_2$ is defined as the length of a linear segment rectangularly lying from the baseline to the point $P_3$, the relationship of $L_1$ and $L_2$ is expressed as $L_1 > 3L_2$. Meeting this condition, the polypropylene composite fiber shows sharp endothermic peak from the low melting component (A), so that the fiber surface stickiness and the decreasing strength can be reduced after the non-woven processing step.

Further in the polyethylene fiber of this invention, the melting points difference of the low melting component (A) and the high melting component is larger, the temperature range of the non-woven fabric procession stage can be made wider, so that the non-woven procession can be easier with a method such as the through-air or the thermal embossing. Especially to addition, decreasing the molting point of the low melting component (A) makes economical advantage as the heat quantity can be reduced to adhere the fiber one another at the non-woven processing stage.

Concerning to the melting points difference between the both components (A) and (B) of the polyethylene fiber of this invention, it is preferably 5° C. or more. (The "Melting point difference" defined in this invention is the temperature difference between the endothermic peaks from the high melting side $P_2$ and the low melting side $P_1$.)

Usually, melting point of resin correlates with its density, density of a resin is lower, its melting temperature is lower. However, a resin having lower density has larger Q value and more increased low molecular weight fraction, so that stickiness of fiber surface and lowered tensile strength of non-woven are problem, while melt starting temperature is lowered.

From such a point of view, it is effective for this invention to comprise the polyethylene (a) polymerized with the metallocene catalyst mainly as the low melting component (A), because the metallocene catalyst is preferable for making the Q value small.

If the polyethylene polymerized with commonly used Ziegler-Natta catalyst is used for the main component of the low melting component (A), observed endothermic peak $P_1$ from the low melting component (A) is broadened on the DSC curve, as shown on FIG. 3. In this case, to make the density of the low melting component (A) higher for making the endothermic peak $P_1$ sharper, the melting point is also higher and the melting points difference between the two components (A) and (B) is smaller. And finally the endothermic $P_1$ from the low melting component (A) is gathered to the endothermic peak $P_2$ from the high melting component (B) to give one unified peak.

Contrary to this, the polyethylene fiber of this invention is using the polyethylene having Q value of 3.0 or less polymerized by the metallocene catalyst for the main component of the low melting component (A). Combining this with the high melting component (B) comprising mainly the polyethylene (b) having the density of 0.940 g/cm³ or more, the DSC curve of the composite fiber shows sharp endothermic peak $P_1$ from the low melting component (A), resolutely separated from the endothermic peak $P_2$ with preferable distance. This suggests that the molecules of the polyethylene (a), which play the part of adhesion component in the low melting component (A) for bonding the fiber one another at the non-woven procession stage, are distributed on high molecular weight side, and the distribution of the polyethylene (a) is narrow. And this also suggests that melting property of both components is resolutely different from each other. As the result, it can be understood that the polyethylene composite fiber having less stickiness and high adhesion strength.

The polyethylene composite fiber of this invention can be produced by conventional melt-spinning method or spun-bonding method. Composite structure of the fiber can be any of a side-by-side, a sheath core, and an eccentric sheath core.

In the case of the polyethylene fiber having the sheath core structure, the weight ratio of the high melting component (B) to the low melting component (A) is 80/20 to 20/80, and 50/50 to 70/30 is more preferable. Concerning to the high melting component (B) being as the core, rigidity of the composite fiber is poorer if decreasing the content of the polyethylene (b) as the main component having the density of 0.940 g/cm³ or more. So that the cardability is worsened, also the processed non-woven fabric become non-bulky and loses good touch feeling. Contrary to this, if the ratio of the low melting component (A) being as the sheath is decreased, the adhesion strength of the composite fiber becomes weak, so that the tensile strength of the obtained non-woven fabric is non-preferably weakened. Therefore the most preferable ratio of the both components is within the range as above mentioned.

The polyethylene composite fiber of this invention may further comprise conventional additive such as an antioxidant, a light resistant, a flame retardant and a pigment, within the range that this invention is effective as aimed.

The polyethylene fiber of this invention may be stretched after melt-spun. Method for the stretching, conventional stretching with heated rolls or stretching in hot water can be applied, and the stretching may be done at one stage, two stages, or multi stages. For obtaining the well-cardable fiber and the bulkier non-woven fabric, it is effective to promote crystal orientation of the fiber to rise its rigidity. For promoting crystal orientation of the fiber, applicable method is high speed drawing at the melt-spinning stage or high ratio stretching at the stretching stage. In the latter case, the stretching ratio is preferably 5 to 8 times at least, and more preferably 10 times or more to obtain the polyethylene composite fiber having high rigidity. Also retention of crimps is important for the polyethylene composite fiber of his invention. In the case of using conventional stuffing box to make the fiber mechanically crimped, it is possible to raise the retention of the crimps by giving sufficient heat to the fiber just before entering it into the stuffing box.

With the polyethylene fiber of this invention, other fibers, which is non-adhesive at the temperature that the fiber of this invention is thermally adhered, can be mixed or combined, within the range that this invention is effective as aimed. Such an other fiber is; for example, a synthetic fiber such as a polypropylene fiber, a polyester fiber, polyamide fiber or a polyacryl vinylon fiber, a regenerated fiber or an animal fiber such as a viscose rayon, a cuprammonium rayon, an acetate, a cotton, a wool, a silk, a hemp or a pulp.

The polyethylene fiber of this invention is suitably used as a raw material for non-woven production. The polyethylene fiber of this invention can be easily processed into the non-woven fabric by conventional method such as embossing, through-air, needle punching, and water-jet entanglement. Especially, the polyethylene fiber of this invention is preferably processed by the thermal bonding method of the embossing and the through-air, as it has the melting temperature difference between the two components and can be thermally treated under wide processing temperature range.

In the case of obtaining the non-woven fabric by the through-air method, if the thermal shrinkage ratio is high, the composite fiber is shrunken under thermal influence at the processing stage, so that some problem arises on the obtained non-woven fabric such as bad dimensional stability, bad quality of the fabric, or shrinkage. Therefore, the web shrinkage (heated in an oven at 120° C.) must be controlled as 15% or less, or more preferably 10% or less.

To control the web shrinkage, it is necessary to rise fluidity of the resin melt-extruded from spinning nozzle. As the method for this, it is applicable that rising the temperature of melted resin at the spinning stage, or using resin having high melt index. Melted polyethylene makes gel (bridged material of thermal degradation) at high temperature, and it causes fiber breakage at the spinning stage. So the latter method is more effective to control the web shrinkage.

As the polyethylene fiber of this invention is less degraded especially under radiation, the obtained non-woven fabric can be widely used for radiology related wear, medical articles such as surgical caps, surgical sheets, surgical covering clothes, surgical gowns and doctor's wear, but the usage is not limited in medical or radiation related area.

EXAMPLES

Hereinafter, this invention is explained more specifically showing the following Examples, but this invention is not limited within these Examples. Concerning to the condition of preparing raw stock, the examination methods and the measurement of each property data in Examples and Comparative Examples, these are also described as the following.

Examples 1 to 6

Comparative Examples 1 to 4

Nine kinds of polyethylene composite fibers were prepared using the low melting component (A) as the sheath, and the high melting component (B) as the core. Table 1 shows the polyethylenes used for each component, and composite ratio (sheath/core ratio).

The low melting component (A) heated at 200° C., and the high melting component (B) heated at 240° C. were extruded from a spinneret having 0.8 mm of spinning holes, then drawn at 376 m/min. of spinning speed, to give an unstretched polyethylene composite fiber having 18.7 dtex of fineness. The obtained unstretched fiber was stretched at 10 times using a hot water stretcher filled with water heated at 90° C., then crimped with a stuffing type crimper to give zigzag crimps, and dried with a hot air suction dryer at 80° C., after it, cut into 51 mm length of staples. Each obtained polyethylene composite fiber according to the above steps had 202 dtex of fineness.

DSC analysis of the polyethylene composite fibers obtained as Examples 1 to 6 and Comparative Example 1 to 4 was done. Analyze condition was according to JIS 7122 using DO Pont's thermal analyzer "DSC 10". The resulted DSC analysis was output of DSC chart so scaled as that the length of 2 W/g scale on the vertical axis (the heat flow) equals to the length of 50° C. scale on the horizontal axis, as each scale being 42 mm, and the lengths of $L_1$, $L_2$ and W (unit: mm) were measured. The result is shown on Table 1.

Using each polyethylene composite fiber obtained as Examples 1 to 6 and Comparative Example 1 to 4, webs having 20 g/m² of basis weight were prepared respectively. The preparation of the webs was done with Yamato Kiko's high speed type sample roller carding machine. In this test, condition of neps appearance and quality of the web were observed, and the cardability of each sample was evaluated according to the following standard. The result is shown on Table 1.

Very Good: Uniformed web was obtained without neps appearance.

Good: Small number of neps was observed but web was uniformed.

Bad: Large number of neps was appeared and web was not uniformed.

Each web obtained from the polyethylene composite fibers of Examples 1 to 6 and Comparative Example 1 to 4 was respectively processed by through-air method to prepare non-woven fabrics of Examples 7 to 12, Comparable Examples 5 to 6.

Condition of the through-air processing was that the thermal adhesion was done using a hot circulation suction band dryer to adhere the polyethylene composite fiber of the web, with blowing 1.0 m/sec. of hot air and at 8.5 m/sec. of processing speed. In this process, the procession temperature was any of 110° C., 115° C., 120° C. and 125° C., as shown on Table 2.

Each web obtained from the polyethylene composite fibers of Examples 1 to 6 and Comparative Example 1 to 4 was respectively processed by thermal embossing method to prepare non-woven fabrics of Examples 13 to 18, Comparable Examples 7 to 9.

Condition of the thermal embossing processing was that the thermal adhesion was done using an embossing processor equipped with a pair of upper and lower rolls to adhere the polyethylene composite fiber of the web, under 1.96 Mpa of line pressure and at 6.0 m/sec. of processing speed. In this process, the procession temperature was any of 105° C., 110° C., 115° C., 120° C. and 125° C., as shown on Table 2.

Each non-woven fabric obtained as Examples 7 to 18 and Comparative Example 5 to 9 was cut at pieces of 15 cm by 5 cm (MD by CD: sample for MD strength test) and 5 cm by 15 cm (MD by CD: sample for CD strength test), breaking tenacity of the non-woven fabric pieces was measured using Shimadzu autograph AG-500D with tensile speed at 200 mm/min. The result is shown on Table 2 and 3.

The touch feeling of each non-woven fabric obtained as Examples 7 to 18 and Comparative Example 5 to 9 was tested. Each non-woven fabric sample was tested by 10 testers, and the touch feeling was reported. The sample reported as being soft by 9 or more testers was estimated as "Very Good", reported as being soft by 5 or 8 testers was estimated as "Good", reported as being soft by 3 or 4 testers was estimated as "Bad", and reported as being soft by 2 or less testers was estimated as "Very Bad". "Very Good" and "Good" samples were decided as being in the level for practical use, and "Bad" and "Very Bad" samples were decided as being out the level for practical use.

Examples 1, 3, 4, and 6 shown on Table 1 are the fibers of this invention having 30/70 of sheath/core ratio, and having different density of the core components. The fibers out of this invention having approximately the same density sheath components as these Examples are also shown as Comparative Examples 1 and 2. These fibers of Examples and Comparative Examples were processed into non-woven fabrics of Example 7, 9, 10 and 12, Comparative Examples 5, 6 respectively (Table 2: Trough-air Non-woven Fabric), and Examples 13, 15, 16, 17, Comparative Example 7, 8, 9 respectively (Table 3: Thermally Embossed Non-woven Fabric). The non-woven tensile strength and touch feeling of Examples was compared with Comparable Examples, as shown on Table 2 and 3.

As the comparison, the non-woven fabrics using the fibers of this invention get good touch feeling and high tensile strength, while those using the fibers out of this invention lose touch feeling and tensile strength. Especially, the fiber of Comparable Example 1 was very sticky at its surface, so that large number of neps appeared at the carding stage, and web collection and non-woven processing was impossible.

Example 2 on Table 1 is the fiber of this invention having the same structure as Example 1, but the sheath/core ratio was changed to 50/50 from 30/70. And Example 5 is the fiber of this invention having the sheath in which a L-LDPE polymerized with Ziegler-Natta catalyst was blended within the range that this invention is effective as aimed. This fiber was processed into a non-woven fabrics of Example 8 (Table 2: Trough-air Non-woven Fabric), and Examples 14, 17 (Table 3: Thermally Embossed Non-woven Fabric). The non-woven tensile strength and touch feeling of Examples was compared with Comparable Examples, as shown on Table 2 and 3. Both non-woven fabrics has good touch feeling and high tensile strength.

Comparable Example 4 on Table 1 is the fiber out of this invention using a L-LDPE polymerized with Ziegler-Natta catalyst as the sheath,having 50/50 of sheath/core ratio. This fiber has small melting point difference, so that it was impossible to be processed into through-air non-woven fabric, and it was processed into an embossed non-woven fabric only at 120° C. of processing temperature as shown in Comparative Example 9 on Table 3, but the obtained non-woven fabric is hard, and has very bad touch feeling.

Example 19

Comparative Example 10

A surface material of a commercially available diaper for adults was cut off, and substituted with the non-woven fabrics of Example 7 and Comparative Example 5 and fixed, as the diapers of Example 19 and Comparative Example 10 respectively. Wearing test was done comparing Example 19 with Comparable Example 5. As the result, it was confirmed that the diaper of Example 19 has good skin contact feeling and tensile strength is high enough for practical use, but that of Comparative Example has bad skin contact feeling and not suitable for practical wearing.

EFFECT OF INVENTION

The polyethylene composite fiber of this invention, its processing temperature range is wide and it is easily processed into non-woven fabric, the obtained non-woven fabric is soft and has high tensile strength. Especially it can be used suitably for a raw stock being processed by the through-air method that has been difficult for polyethylene fiber processing. It is suitably used not only for medical material, but also for hygienic material and others.

TABLE 1

|  |  | Catalyst | Density (g/cm³) | Q Value | MFR (g/10 min) | S/C Ratio | Cardability | Web Shrinkage (%) | $L_1$ | $L_2$ | W |
|---|---|---|---|---|---|---|---|---|---|---|---|
| Example 1 | Sheath | Metallocene | 0.910 | 1.9 | 30 | 30/70 | Good | 4.4 | 19 | 3 | 2 |
|  | Core | Ziegler-Natta | 0.965 | 4.2 | 40 |  |  |  |  |  |  |
| Example 2 | Sheath | Metallocene | 0.910 | 1.9 | 30 | 50/50 | Good | 9.7 | 20 | 6 | 6 |
|  | Core | Ziegler-Natta | 0.965 | 4.2 | 40 |  |  |  |  |  |  |
| Example 3 | Sheath | Metallocene | 0.915 | 1.8 | 25 | 30/70 | Good | 8.4 | 22 | 3 | 3 |
|  | Core | Ziegler-Natta | 0.955 | 4.0 | 16 |  |  |  |  |  |  |
| Example 4 | Sheath | Metallocene | 0.925 | 2.0 | 25 | 30/70 | Good | 4.5 | 29 | 4 | 6 |
|  | Core | Ziegler-Natta | 0.965 | 4.2 | 40 |  |  |  |  |  |  |
| Example 5 | *Sheath | Metallocene | 0.910 | 1.7 | 25 | 50/50 | Good | 8.8 | 38 | 5 | 10 |
|  |  | Ziegler-Natta | 0.935 | 5.2 | 20 |  |  |  |  |  |  |
|  | Core | Ziegler-Natta | 0.965 | 4.2 | 40 |  |  |  |  |  |  |
| Example 6 | Sheath | Metallocene | 0.860 | 2.5 | 25 | 30/70 | Good | 10.5 | 15 | 6 | 6 |
|  | Core | Ziegler-Natta | 0.955 | 4.0 | 16 |  |  |  |  |  |  |
| Comparative Example 1 | Sheath | Ziegler-Natta | 0.910 | 4.5 | 20 | 30/70 | Bad | 26.3 | 4 | 3.5 | — |
|  | Core | Ziegler-Natta | 0.955 | 4.0 | 16 |  |  |  |  |  |  |
| Comparative Example 2 | Sheath | Ziegler-Natta | 0.915 | 4.3 | 25 | 30/70 | Bad | 29.9 | 7 | 5 | — |
|  | Core | Ziegler-Natta | 0.955 | 4.0 | 16 |  |  |  |  |  |  |
| Comparative Example 3 | Sheath | Ziegler-Natta | 0.920 | 4.7 | 30 | 30/70 | Good | 24.5 | 17 | 16.5 | — |
|  | Core | Ziegler-Natta | 0.955 | 4.0 | 16 |  |  |  |  |  |  |
| Comparative Example 4 | Sheath | Ziegler-Natta | 0.935 | 5.0 | 25 | 50/50 | Bad | 32.3 | 39 | 21 | — |
|  | Core | Ziegler-Natta | 0.955 | 4.0 | 16 |  |  |  |  |  |  |

*Example 5: Blending ratio of the Sheath is 50/50

TABLE 2

Trough-air Non-woven Fabric

|  | Processing Temperature (°C.) | Tensile Strength (N/5 cm) MD | Tensile Strength (N/5 cm) CD | Touch Feeling |
|---|---|---|---|---|
| Example 7 | 110 | 46.6 | 3.5 | Very Good |
|  | 115 | 65.4 | 5.0 | Very Good |
|  | 120 | 80.6 | 8.5 | Good |
| Example 8 | 110 | 55.2 | 6.3 | Very Good |
|  | 115 | 70.9 | 6.9 | Very Good |
|  | 120 | 88.8 | 10.2 | Good |
| Example 9 | 110 | 43.2 | 3.7 | Very Good |
|  | 115 | 66.7 | 5.0 | Very Good |
|  | 120 | 87.3 | 9.4 | Good |
| Example 10 | 115 | 49.3 | 4.0 | Very Good |
|  | 120 | 70.9 | 5.8 | Very Good |
|  | 125 | 88.8 | 8.3 | Good |
| Example 11 | 110 | 39.2 | 2.9 | Good |
|  | 115 | 60.3 | 4.8 | Good |
|  | 120 | 81.5 | 8.3 | Bad |
| Example 12 | 90 | 40.2 | 3.0 | Good |
|  | 95 | 45.3 | 8.9 | Good |
|  | 100 | 60.0 | 4.8 | Bad |
| Comparative Example 5 | 115 | 29.4 | 2.6 | Bad |
|  | 120 | 55.0 | 4.2 | Very Bad |
| Comparative Example 6 | 115 | 19.0 | 1.7 | Good |
|  | 120 | 62.8 | 4.7 | Bad |

TABLE 3

Thermally Embossed Non-woven Fabric

|  | Processing Temperature (°C.) | Tensile Strength (N/5 cm) MD | Tensile Strength (N/5 cm) CD | Touch Feeling |
|---|---|---|---|---|
| Example 13 | 105 | 90.7 | 16.0 | Very Good |
|  | 110 | 95.3 | 19.7 | Very Good |
|  | 115 | 100.4 | 20.2 | Good |
| Example 14 | 105 | 88.4 | 16.4 | Very Good |
|  | 110 | 98.4 | 18.9 | Very Good |
|  | 115 | 109.3 | 22.3 | Good |
| Example 15 | 110 | 50.2 | 11.3 | Very Good |
|  | 115 | 110.0 | 19.0 | Good |
|  | 120 | 113.0 | 20.5 | Good |
| Example 16 | 120 | 94.4 | 15.3 | Very Good |
|  | 125 | 115.5 | 17.3 | Good |
| Example 17 | 110 | 81.8 | 10.3 | Good |
|  | 115 | 106.2 | 19.3 | Good |
|  | 120 | 108.9 | 20.7 | Good |
| Example 18 | 85 | 70.4 | 5.9 | Good |
|  | 90 | 87.3 | 14.3 | Good |
|  | 95 | 93.0 | 18.0 | Good |
| Comparative Example 7 | 110 | 39.5 | 6.8 | Bad |
|  | 115 | 70.4 | 13.6 | Very Bad |
|  | 120 | 73.8 | 14.7 | Very Bad |
| Comparative Example 8 | 110 | 25.0 | 4.0 | Very Bad |
|  | 115 | 75.0 | 13.5 | Very Bad |
| Comparative Example 9 | 120 | 72.2 | 7.4 | Very Bad |

What is claimed is:

1. A polyethylene composite fiber comprising two kinds of polyethylene resin components having different melting points, wherein the low melting component (A) comprises a polyethylene (a) polymerized with a metallocene catalyst, and having a density of 0.850 to 0.930 g/cm³ and a Q value (number average molecular weight/weigh average molecular weight) of 3.0 or less, and the high melting component (B) is a polyethylene (b) having a density of 0.940 g/cm³ or more.

2. A polyethylene composite fiber comprising two kinds of polyethylene resin components having different melting points, wherein the low melting component (A) comprises a polyethylene (a) polymerized with a metallocene catalyst, and having a density of 0.850 to 0.930 g/cm³ and a Q value (number average molecular weight/weigh average molecular weight) of 3.0 or less, and the high melting component (B) is a polyethylene (b) having a density of 0.940 g/cm³ or more, and analysis of the fiber using a differential scanning calorimeter (DSC) shows two different endothermic peaks $P_1$ and $P_2$ on the DSC curve from the two components (A) and (B) of the fiber respectively, and when $L_1$ is defined as the length from the baseline of the DSC curve to the endothermic peak $P_1$, and when W is defined as the length of a linear segment parallel with the baseline, passing the midpoint between the baseline and $P_1$, and crossing the DSC curve, the relationship of $L_1$ and W is expressed as $L_1>3W$, on the proviso that a programming rate is 10° C./min., and the DSC chart is so scaled as that the length of 2 W/g scale on the vertical axis (the heat flow scale, unit: W/g) equals to the length of 50° C. scale on the horizontal axis (the temperature scale, unit: ° C.).

3. The polyethylene composite fiber according to claim 2, wherein $P_3$ is defined as a point being on the DSC curve between the two endothermic peaks $P_1$ and $P_2$ of the two components and being closest to the baseline, and $L_2$ is defined as the length of a linear segment rectangularly lying from the baseline to the point $P_3$, the relationship of $L_1$ and $L_2$ is expressed as $L_1>3L_2$.

4. The polyethylene composite fiber according to claim 2, wherein the polyethylene (b) of the high melting component (B) is a high density polyethylene having a density of 0.945 g/cm³ to 0.965 g/cm³.

5. The polyethylene composite fiber according to claim 2, wherein the polyethylene (b) of the high melting component (B) is a polyethylene having a melting point of 125° C. to 135° C.

6. The polyethylene composite fiber according to claim 2, wherein the polyethylene (b) of the high melting component (B) is a polyethylene having a melt flow index of 5 g/10 min. to 45 g/10 min.

7. The polyethylene composite fiber according to claim 2, wherein the polyethylene (a) of the low melting component (A) is a polyethylene having a density of 0.850 g/cm³ to 0.930 g/cm³.

8. The polyethylene composite fiber according to claim 2, wherein the polyethylene (a) of the low melting component (A) is a polyethylene having a melting point of 70° C. to 125° C.

9. The polyethylene composite fiber according to claim 2, wherein the polyethylene (a) of the high melting component (A) is a polyethylene having a melt flow index of 5 g/10 min. to 45 g/10 min.

10. The polyethylene composite fiber according to claim 2, wherein the melting point difference of the two components is 5° C. or more.

11. A non-woven fabric using the polyethylene composite fiber according to claim 1.

12. A non-woven fabric using the polyethylene composite fiber according to claim 2.

13. The non-woven fabric according to claim 12, wherein the non-woven fabric is obtainable with spun bonding method.

14. The non-woven fabric according to claim 12, wherein the non-woven fabric is obtainable with through air processing method that the fiber is thermally melt-bonded one another.

15. The non-woven fabric according to claim 12, wherein the non-woven fabric is obtainable with point bonding method that the fiber is thermally melt-bonded one another.

16. A medical article using the non-woven fabric according to claim 12.

17. A sanitary article using the non-woven fabric according to claim 12.

* * * * *